United States Patent [19]
Peter et al.

[11] Patent Number: 5,434,280
[45] Date of Patent: Jul. 18, 1995

[54] PROCESS FOR PREPARING PURE MONOGLYCERIDES, PURE DIGLYCERIDES AND/OR PURE TRIGLYCERIDES

[75] Inventors: Siegfried Peter, Lindenweg 3, D-8525 Uttenreuth-Weiher; Bernd Czech, Erlangen; Ulrich Ender, Erlangen; Eckhard Weidner, Erlangen, all of Germany

[73] Assignee: Siegfried Peter, Uttenreuth-Weiher, Germany

[21] Appl. No.: 155,923

[22] Filed: Nov. 22, 1993

Related U.S. Application Data

[63] Continuation of Ser. No. 580,196, Sep. 10, 1990.

[30] Foreign Application Priority Data

Sep. 8, 1989 [DE] Germany .................. 39 30 026.9

[51] Int. Cl.⁶ .............................................. C11B 7/00
[52] U.S. Cl. ................................... 554/205; 554/206; 554/210
[58] Field of Search .................. 554/206, 205, 210

[56] References Cited

U.S. PATENT DOCUMENTS 4,345,976 8/1982 Peter et al. .................. 554/210

*Primary Examiner*—José G. Dees
*Assistant Examiner*—Deborah D. Carr
*Attorney, Agent, or Firm*—Horst M. Kasper

[57] ABSTRACT

The invention relates to a process for recovering monoglycerides and optionally diglycerides and/or triglycerides as well as optionally glycerol from mixtures comprising glycerides and glycerol containing glycerides, respectively, by countercurrent extraction with a circulating extraction. As an extractant, forming a separate phase, there is used a hydrocarbon having a density of more than 180 kg/m³ and/or trifluoromethane having a density of more than 180 kg/m³.

37 Claims, 4 Drawing Sheets

PROCESS FOR PREPARING PURE MONOGLYCERIDES, PURE DIGLYCERIDES AND/OR PURE TRIGLYCERIDES

This is a continuation of application Ser. No. 07/580,196, filed Sep. 10, 1990, now pending.

BACKGROUND OF THE INVENTION

1. Field of the invention

The invention relates to a process for separating pure monoglycerides, pure diglycerides, and/or pure triglycerides.

2. Brief Description of the Background of the Invention Including Prior Art

Monoglycerides and diglycerides are partial esters of glycerol with higher molecular fatty acids. Commercially available monoglycerides consist of mixtures of monoesters and diesters including minor proportions of triesters. As the monoesters and diesters of glycerol are edible, they are used in various fields of the foodstuff industry, pharmaceutical, and cosmetics industry because of their emulsifying, stabilizing, plasticizing, and thickening characteristics. For many purposes, particularly technical ones, the equilibrium mixture obtained on preparation of the glycerides may be used directly following separation of the non-reacted glycerol. In other fields of use, however, preparation of high-percentage monoglycerides and diglycerides is desired. Monoglycerides, prepared by molecular distillation and having a monoglyceride content of more than 90% are used mainly in the foodstuff industry (noodles, pastries, sweets and baking aids, margarine, ice cream).

Through addition of monoglyceride (up to 5% of palmitic acid/stearic acid monoglyceride of 90% purity, or 10% of palmitic acid/stearic acid mono/diglyceride), one achieves self-emulsifying characteristics of shortenings intended for baking purposes (superglycerolated shortenings).

The term "shortening" literally means making something shorter and is derived from the baking characteristics of these substances. Due to their specific structure, the monoglycerides are capable of altering the plasticizing effect of starch and gluten during preparation of the dough by inserting themselves in finely divided form into the homogeneous plasticized materials, thus breaking them up and making the dough smoother, i.e. shorter. At the same time, they facilitate the incorporation of air. As a consequence, there are obtained bakery products of increased volume and improved "shortness".

The essential components of margarine are edible fats and oils, drinking water, and emulsifiers. As emulsifiers, there may be used lecithin, egg yolks and/or monoglycerides and diglycerides of edible fatty acids. Margarine may also comprise taste and smell-improving additives (flavors), sour milk, skim milk, salt, starch syrup, citric acid and/or other edible acids, vitamins, as well as officially approved food colors (usually carotin or carotin-containing oils). Emulsifiers are mandatory adjuvants in the preparation of margarine as they render possible the formation of water-in-oil emulsions. Most commonly used are monoglycerides and vegetable lecithin as they assist each other in their emulsifying action. Used in practice are products comprising about 40% and about 90%, respectively, of monoglycerides of $C_{16}/C_{18}$-acids (palmitic acid, stearic acid, also in admixture with oleic acid) and, in addition thereto, 60% and 10%, respectively, of diglycerides. Common are additions of up to 0.5% and 0.25%, respectively, corresponding to about 0.2% of monoglyceride based on the fatty phase. Higher proportions of emulsifier are usually required for the preparation of low-calorie margarine.

Monoglycerides and diglycerides may be obtained by esterifying glycerol with fatty acids. By transesterification of triglycerides with glycerol or reaction of glycerol with fatty acids in the presence of catalysts, there are obtained mixtures composed of glycerol, mono-, di-, and triglycerides, and free fatty acids. A lately introduced technique is enzymatic cleavage of triglycerides. Each of the above methods produces a mixture of monoglycerides, diglycerides, and triglycerides. On esterification, for instance, there is obtained an equilibrium mixture which, after separation of the glycerol, comprises 60% of monoglycerides, 35% of diglycerides, and 5% of triglycerides. The starting mixture for esterification is chosen in such a way that monoglycerides are produced as the main product in the equilibrium mixture. The mixture is usually separated by molecular distillation. At the high temperatures within the film evaporator, a slight degree of disproportioning is encountered so that the monoglycerides or diglycerides contain small amounts of the other two esters as well as traces of free fatty acids. Moreover, the ratio of 1-monoglycerides to 2-monoglycerides is shifted in favor of the 2-monoglycerides.

Due to the disproportioning taking place at the temperatures within the film evaporator, monoglycerides having a purity above 95% cannot be produced economically by molecular distillation. There does, however, exist a wide interest in monoglycerides having a purity of 99% or more.

It is known that monoglycerides may be separated from a mixture of mono-, di-, and triglycerides with the aid of dense carbon monoxide. Required for the above method are, however, pressures of more than 350 atm. at temperatures of 40° C. Moreover, even at pressures of 350 atm., loading is so low (less than 0.5%) to make economic recovery of high-percentage monoglycerides impossible.

Proposed in the German Patent application laid open DE-OS 23 40 566 is the use of acetone as an entrainer. Here, the monoglycerides as the more easily soluble components enter into the head product during countercurrent extraction. But the separating factors are relatively low so that recovery of pure monoglycerides is not interesting under economic aspects, especially as the loadings of from 0.5% to 1.5% thus achieved are quite small. Moreover, separation of the acetone entrainer from the product is involved and time-consuming.

The use of hydrocarbons as a cosolvent for a supercritical extractant such as carbon dioxide, $N_2O$, sulfurhexafluoride, trifluoromethane or tetrafluoromethane was proposed in German Patent reference P 38 25 248. This process does not suffer from the above disadvantages. However, cosolvent (entrainer) and supercritical component are not evenly distributed over fluid and liquid phases. Thus, on withdrawal of the products, different quantities of cosolvent and supercritical component will be removed from the extractant to be recycled. Thus, the composition of the extractant must be continuously corrected with the aid of a somewhat complex control and analyzing device.

SUMMARY OF THE INVENTION

Purposes of the Invention

It is now the object of the invention to provide a process for recovering pure monoglycerides and pure diglycerides in a simplified and more economical manner.

The above object is surprisingly achieved by the process according to the invention.

These and other objects and advantages of the present invention will become evident from the description which follows.

Brief Description of the Invention

The present invention provides a process for recovering monoglycerides and optionally diglycerides and/or triglycerides as well as optionally glycerol from mixtures of glycerides and, respectively, glycerol-containing glycerides by countercurrent extraction with a recycled extractant. Said process is characterized in that hydrocarbon, having a density of more than 180 kg/m$^3$, and/or trifluoromethane having a density of more than 180 kg/m$^3$ is (are) used as an extractant capable of forming a separate phase.

In the process according to the invention, temperature and pressure are chosen such that the system of the mixture of glycerides or glycerol-containing glycerides and the extractant is present as a two-phase system in separating column and fractionating columns. This will be the case when the density of the highly volatile hydrocarbons, having 2 to 5 carbon atoms, is within the range of from 180 to 800 kg/m$^3$. At higher densities, the system of glyceride mixture and hydrocarbon will be present in a single phase, thus making separation impossible. At lower densities, loading of the extractant will be too low for economic operation.

Surprisingly, it has been found that the proposed density range permits working conditions wherein, on the one hand, the system of mixed glycerides and highly volatile hydrocarbon is a two-phase system while, on the other hand, loading of the extractant at adequate separating factors makes economic working feasible.

In the process of the invention, no supercritical component of poor solubility, such as $CO_2$, need be added to form a two-phase system.

The novel features which are considered as characteristic for the invention are set forth in the appended claims. The invention itself, however, both as to its method of operation, its products and physical requirements, together with additional objects and advantages thereof, will be best understood from the following description of specific embodiments, examples, and accompanying drawings.

DESCRIPTION OF INVENTION AND PREFERRED EMBODIMENTS

Figure 1:
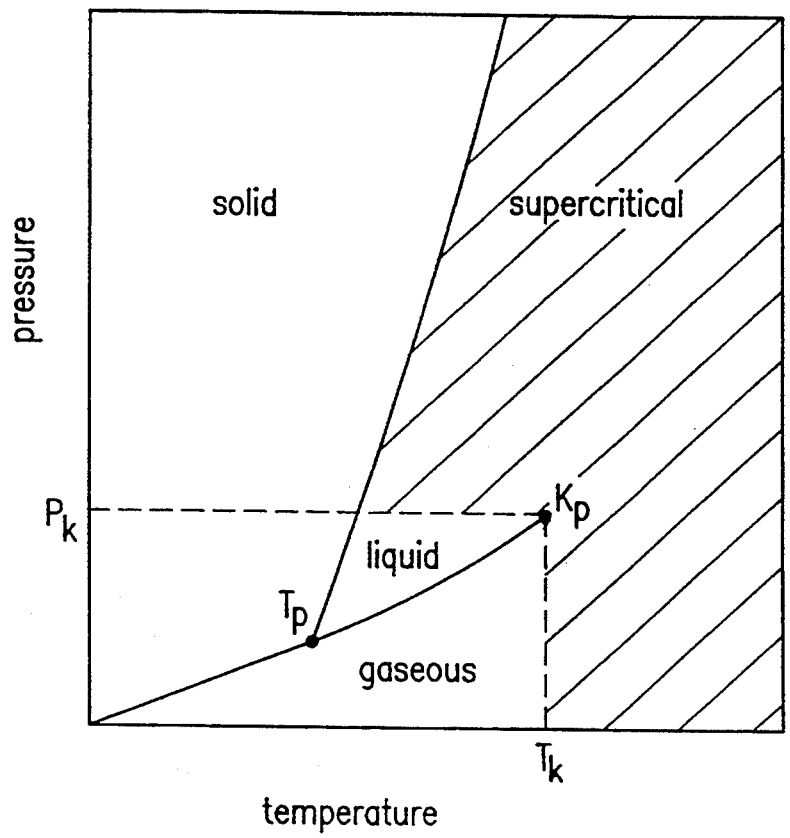
FIG. 1 is a diagram showing the relationship pressure/temperature.

According to the process of the invention, high separating factors in combination with relatively high loadings may be realized by using low molecular hydrocarbons such as ethane, propane, butane, pentane, ethene, propene, butene, as well as trifluoromethane, or mixtures thereof as supercritical extractants. To be regarded as supercritical is any substance, the temperature of which at the respective pressures is higher than the critical temperature, or the pressure of which at the respective temperature is higher than the critical pressure; see the shaded area in FIG. 1. Working preferably takes place in the so-called "near-critical" state. "Near-critical" are working conditions wherein pressure and temperature are chosen to be close to the boundaries of the shaded area in FIG. 1. For instance, working at a temperature below critical temperature is possible also when the chosen pressure is above critical pressure.

The preferred density range in the working method of the invention is from 200 to 800 kg/m$^3$ for hydrocarbons and from 300 to 1100 kg/m$^3$ for trifluoromethane.

In the mentioned density range, the separating factors between monoglycerides and diglycerides, or between diglycerides and triglycerides, are so high that separation of monoglycerides, diglycerides, and triglycerides from the mixture of glycerides is possible in a single operation. Also possible within this density range is the separation of mixed glycerol-containing glycerides into glycerol, monoglycerides, diglycerides, and triglycerides.

Another essential advantage of the process according to the invention is the low thermal stress to which the products are subjected. Separation of e.g. glycerides of $C_{18}$ and $C_{16}$ acids through molecular distillation requires temperatures of about 200° C. in the evaporator. In contrast thereto, the temperatures in "near-critical fluid extraction" are the melting temperatures of the glycerides. For instance, glycerides of stearic acid melt between 70° and 80° C. Thus, separation of the glycerides of stearic acid may take place at temperatures of from 90° to 110° C. Glycerides of oleic acid have a melting point around 30° C. For their separation, a temperature between 40° and 60° C. will therefore be preferred. The low temperatures required in the process of the invention greatly reduce the risk of glyceride disproportioning commonly encountered in molecular distillation so that products, having a monoglyceride content of 99 to 99.5%, may be obtained.

On use of e.g. ethane as an extractant, suitable working conditions for the separation of mixed glycerides or glycerol-containing glycerides are temperatures of from 10° to 120° C., preferably from 20° to 80° C., as well as pressures of from 50 to 500 bar, preferably from 100 to 350 bar.

The density of ethane at e.g. 20° C. and a pressure of 300 atm. is 450 kg/m$^3$. The loading of ethane in equilibrium with a glyceride mixture comprising 59% by weight of monoglycerides, 36% by weight of diglycerides, 4.6% by weight of triglycerides of oleic acid and 0.4% by weight of free fatty acids is 1% by weight under the mentioned conditions. By raising the temperature to about 100° C. and lowering the pressure to about 50 atm., loading on regeneration of the extractant may be reduced to a value below 0.02§ by weight.

Temperatures of from 40° to 150° C., preferably from 60° to 120° C., and pressures of from 40 to 350 bar, preferably from 70 to 250 bar, are appropriate when propane is used as an extractant.

At e.g. 110° C. and a pressure of 85 bar, propane has a density of 360 kg/m$^3$. Under these conditions, the loading of propane in equilibrium with a glyceride mixture, comprising 61% by weight of monoglycerides, 35% by weight of diglycerides, 3.5% by weight of triglycerides of stearic acid, and 0.5% by weight of fatty acids, amounts to 5.4% by weight. By raising the temperature to about 120° C. and lowering the pressure to about 35 bar, loading on regeneration of the extractant may be reduced to a value of less than 0.04% by weight.

But even below the critical temperature which, in the case of propane, is 80° C., the monoglycerides can be separated from a mixture of glycerides. At 80° C. and a pressure of 60 bar, propane has a density of 410 kg/m$^3$. The loading of propane in equilibrium with a glyceride mixture, comprising 61% by weight of monoglycerides, 35% by weight of diglycerides, 3.5% by weight of triglycerides of stearic acid, and 0.5% by weight of free fatty acids, will be 6% by weight under the mentioned conditions. By raising the temperature to about 110° C. and lowering the pressure to about 30 bar, loading can be reduced to a value of less than 0.02% by weight. Under these conditions, the density of propane is 57 kg/m$^3$.

In general, it may be said that the density of the extractants is reduced for their regeneration to one fifth to one seventh of the original value.

In the process of the invention and in contrast to the process described in DE-OS 23 40 566, the monoglycerides are not found in the head product but constitute the bottom product in the countercurrent column, hereinafter referred to as the separating column. As an extract, the extractant at the head of the column contains the diglycerides and triglycerides which may subsequently be separated from the extractant by fractionated precipitation. For fractionated precipitation, two fractionating columns may be used. If fractionated separation of the diglycerides and triglycerides is dispensed with, a single fractionating column will be sufficient. In the separating column as well as in the fractionating columns, two phases are present. Between the head of the separating column and the relief valve, the circulating extract is in the form of a single phase. On pressure release, the dissolved components precipitate as a liquid phase. The resulting liquid phase is separated in the fractionating columns. Thereafter, the circulating extractant is present as a single phase.

In one embodiment of the process according to the invention, wherein the extractant flows from the bottom to the top of a countercurrent column and the mixed glycerides to be separated are fed into the middle or at the top of the column, the liquid phase flows downwards in a countercurrent. On the way down, the latter is depleted of diglycerides and triglycerides so that finally a bottom product, having a monoglyceride content above 99%, is obtained. The extractant, leaving the head of the respective column, carries along any diglycerides and triglycerides contained in the feed as well as traces of monoglycerides. After the density has been reduced, e.g. through lowering of the pressure and/or raising of the temperature, the extractant, leaving the separating column, is fed approximately into the middle of the subsequent column, hereinafter called fractionating column. Due to the density reduction, the diglycerides are preferably precipitated in that fractionating column and will flow downwards as a liquid phase. On its way down, the precipitated liquid is depleted of triglycerides, the resulting bottom product thus having a high content of diglycerides. Part of the bottom product from the fractionating column may be recycled to the separating column, the remainder being withdrawn as a product comprising diglycerides of high purity.

The extractant leaving the head of the fractionating column comprises any triglycerides contained in the feed as well as a small amount of diglycerides. After further reduction of the density, the extractant, leaving the fractionating column, is fed into the middle section of a third column, hereinafter called regenerating column. Due to the density reduction, any difficultly volatile substances still dissolved in the extractant are precipitated in the regenerating column to an essentially complete extent to flow downwards as a liquid phase. Part of the glycerides precipitated in the regenerating column may be recycled to the fractionating column, the rest being withdrawn as a product mainly consisting of triglycerides.

Part of the cycle gas, i.e. of the extractant regenerated in the regenerating column, is again fed into the bottom of the separating column following an appropriate density increase accomplished by raising the pressure and/or lowering the temperature, where the extractant flows from the bottom to the top of the respective column. Likewise, some part of the regenerated extractant may be fed into the bottom of the fractionating column after an appropriate raise in density.

In this manner, the process of the invention permits separation of a mixture of monoglycerides, diglycerides, and triglyceride in a single operation to produce three fractions either containing monoglycerides, diglycerides, or triglycerides of high purity without requiring the use of a complex control and analyzing device for continuously correcting the composition of the extractant.

Figure 2:
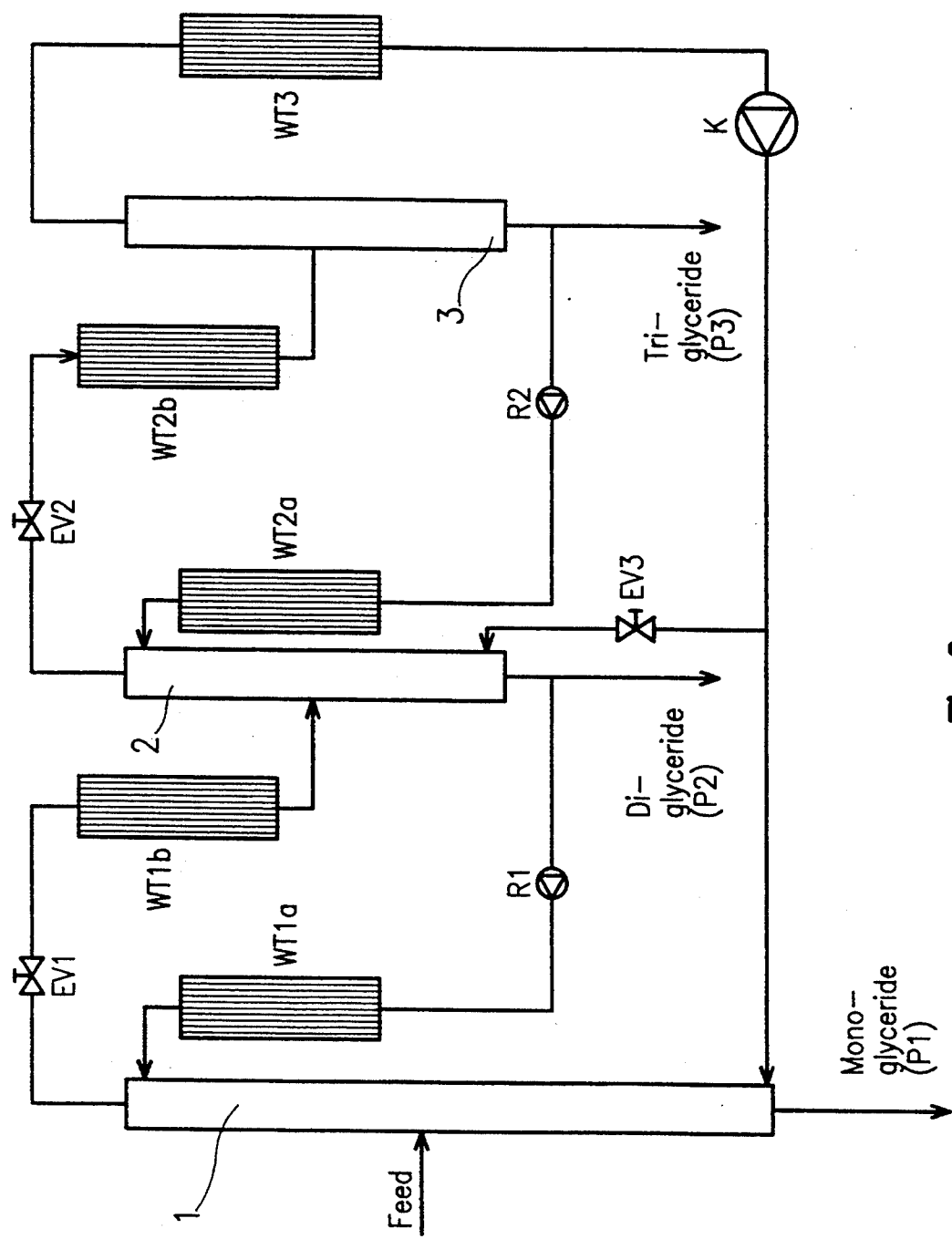
FIG. 2 is a schematic representation of a first embodiment of the invention process.

The process of the invention is now illustrated by means of the embodiment schematically represented in FIG. 2. The apparatus shown in FIG. 2 comprises three columns, of which one, namely the separating column 1, serves for separating the monoglycerides from the mixture of glycerides. The monoglycerides are obtained as a bottom product. The second column is a fractionating column 2 for separating diglycerides of high purity. The third column, i.e. the regenerating column 3, serves for separating the remaining extracted components from the cycle gas. The mixture of glycerides previously freed of glycerol is fed into the middle section of the separating column. In the separating column, the circulating extractant is loaded preferably with diglycerides and triglycerides. At the same time, the extractant dissolves in the downward flowing liquid phase which gradually gets enriched in monoglycerides.

The extractant loaded with the more easily soluble components, i.e. diglycerides and triglycerides, leaves the amplifying section of separating column 1 at the head. The loaded extractant is expanded via pressure relief valve EV1 and, after having passed through heat exchanger WT1$b$, is fed into the middle section of fractionating column 2. To alter the density, pressure and temperature in the fractionating column 2 are adjusted such that preferably diglycerides as well as the minor residue of monoglycerides are separated. The condensed phase is withdrawn from the bottom of the fractionating column 2 and divided into product P2 and recycle stream R1. The recycle stream R1 is passed through heat exchanger WT1$a$ and fed into the head of separating column 1.

The stream of extractant from fractionating column 2, loaded predominantly with triglycerides, is expanded via pressure relief valve EV2 and passes through heat exchanger WT2b into the regenerating column 3. Density is reduced in the regenerating column 3 by a change in pressure and/or temperature so that the extractant leaving the column is free of difficultly volatile components. The condensed phase, containing free fatty acids and minor amounts of diglycerides besides triglycerides, is withdrawn from the bottom of regenerating column 3 and divided into product P3 and recycle stream R2. The recycle stream R2 from regenerating column 3 passes through heat exchanger WT2a to be fed into the head of fractionating column 2.

The regenerated extractant leaves the regenerating column 3 at the head and, after having passed through heat exchanger WT3, is recycled into the separating column 1 by means of compressor K. A smaller part of the regenerated cycle gas is partially expanded through pressure relief valve EV3 and fed into the bottom of fractionating column 2.

Recovered as a bottom product from fractionating column 2 are high-percentage diglycerides, while the bottom product from regenerating column 3 is rich in triglycerides. The three different bottom products thus obtained are continuously withdrawn and collected in containers under expansion. The quantities of gaseous extractant thus released are fed back into the cycle gas by means of a compressor.

When fractionation of the components dissolved in the extractant is conducted under isothermal conditions, the pressure in fractionating column 2 is reduced by about 5 to 60 bar, preferably by 15 to 40 bar, as compared to the pressure in separating column 1. Fractionation may also be conducted under isobaric conditions. In that case, the temperature in fractionating column 2 is raised by 10° to 80° C., preferably by 20° to 50° C. over the temperature in separating column 1. Also possible is a combination of pressure reduction and increase in temperature. The extractant is regenerated either by expansion alone or by expansion and simultaneous increase in temperature. The pressure during regeneration is 25 to 80 bar in a temperature range of from 40° to 120° C.

To prevent formation of a single phase in the separating column due to the decreasing content of monoglycerides in the amplifying section of separating column 1, it is advisable to raise the temperature towards the head of the column. Depending on the composition of the mixture of glycerides with respect to the involved fatty acids, a temperature difference between head and bottom of the column of from 5° to 30° C., preferably of from 10° to 20° C., is advantageous. Moreover, it is advisable to provide for a temperature gradient between head and bottom of fractionating column 2. In that case, the temperature difference between head and bottom is from 5° to 40° C., preferably from 10° to 30° C.

Figure 3:
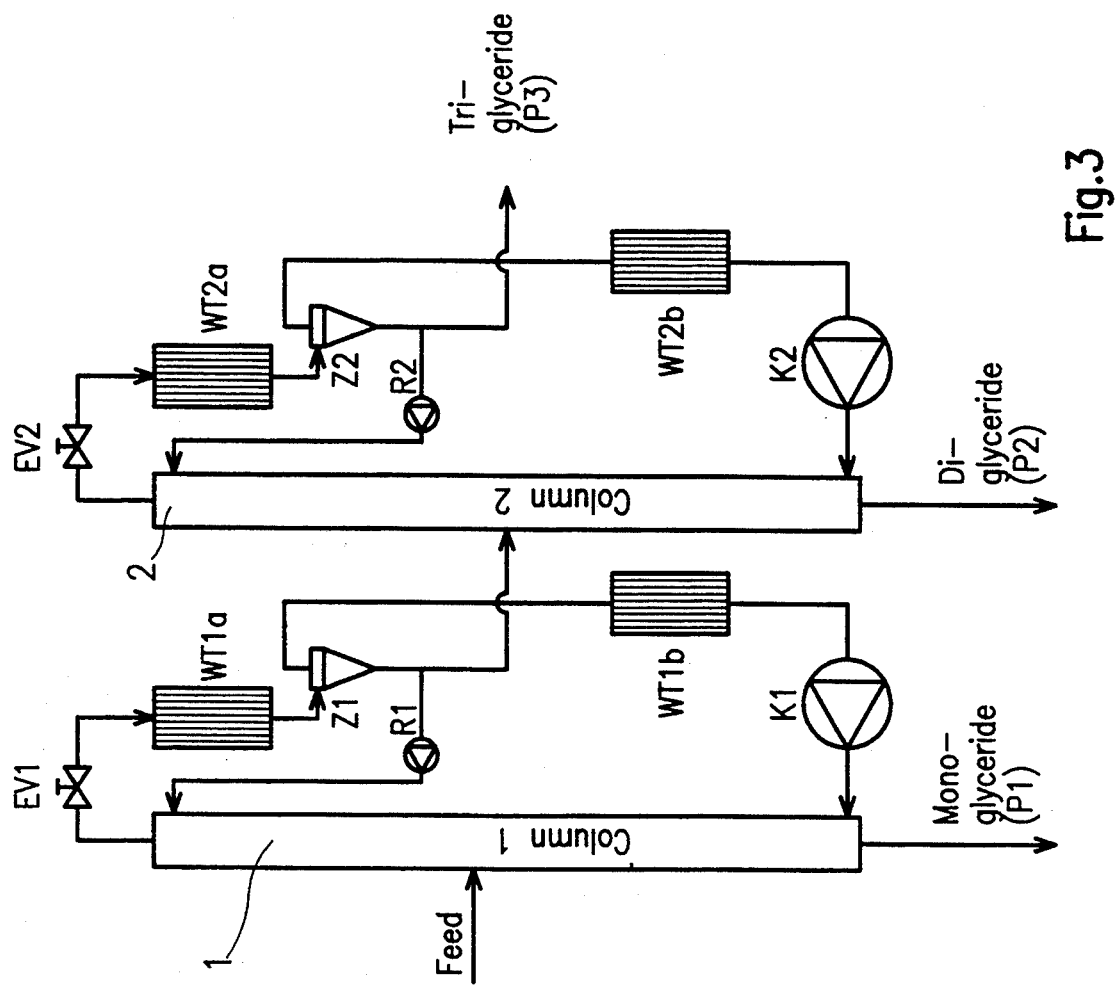
FIG. 3 is a schematic representation of a second embodiment of the invention process.

Another embodiment of the process according to the invention is schematically represented in FIG. 3. Here, the apparatus comprises two countercurrent columns with separate closed cycles in cascade or series connection. The glycerol-containing mixture of glycerides is fed into the middle section of the first column 1. The chosen operating conditions are such that the circulating extractant preferably dissolves the diglycerides and triglycerides. At the same time, the extractant dissolves in the downward flowing liquid which gradually becomes enriched in glycerol and monoglycerides. Obtained as a bottom product is a mixture of glycerol and monoglycerides. Glycerol may be separated from the monoglycerides by washing with water or vacuum distillation.

The extractant loaded with diglycerides and triglycerides is expanded in a pressure relief valve EV1 and heated in heat exchanger WT1a. The dissolved diglycerides and triglycerides are thus precipitated. They are separated from the extractant stream in cyclone separator Z1. The extractant, freed of liquid droplets, passes through heat exchanger WT1b and is fed back by means of cycle gas compressor K1 into column 1 at a point above the bottom section. Part of the product, separated in cyclone separator Z1, is fed as a recycle stream R1 into the head of column 1, the remainder being transferred to column 2.

Pressure and temperature in column 2 are chosen such that the triglycerides are separated as a head product. The extractant loaded with triglycerides leaves column 2 at the head, is expanded in pressure relief valve EV2 and heated in heat exchanger WT2a. The triglycerides dissolved in the extractant are thereby precipitated. In cyclone separator Z2, the precipitated triglycerides of high purity are separated from the extractant. The regenerated extractant passes through heat exchanger WT2b and is recycled by means of cycle gas compressor K2 into column 2 at a point above the bottom section. The liquid separated in the cyclone separator Z2 is divided into a recycle stream R2 for column 2 and product P3. The recycle stream R2 is fed back into column 2. The bottom product P2 from column 2 consists of diglycerides recovered in high purity.

Figure 4:
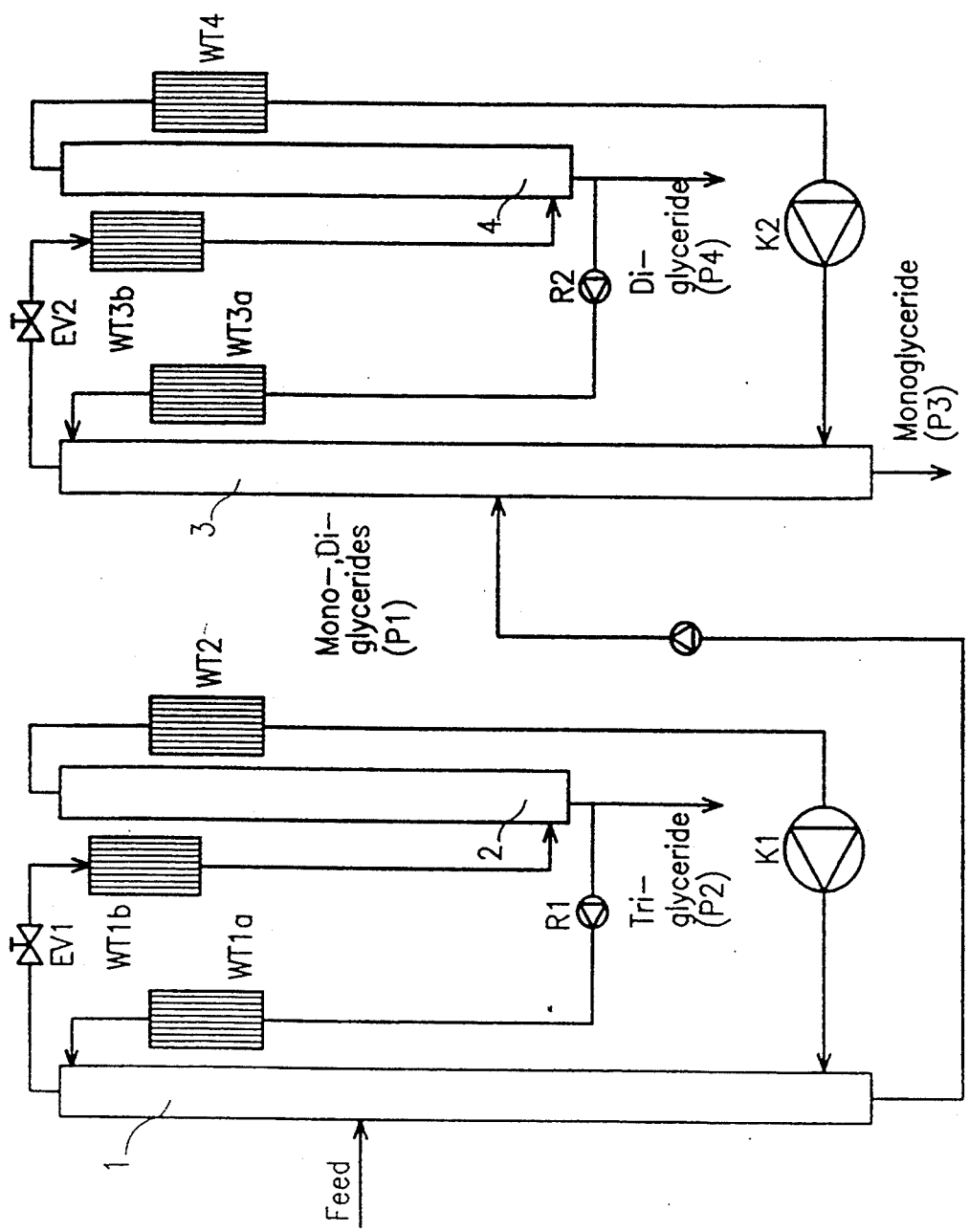
FIG. 4 is a schematic representation of a third embodiment of the invention process.

Still another embodiment of the process according to the invention is shown in FIG. 4. Here, the apparatus comprises the separating column 1, regenerating column 2, a further separating column 3 and a regenerating column 4. The feed, previously freed of glycerol by washing with water or distillation, is fed into the middle section of column 1. Pressure and temperature are chosen such that the triglycerides may be withdrawn together with the extractant from the head of the column. The extractant, loaded with triglycerides, leaves the head of column 1 and is expanded in pressure relief valve EV1 as well as heated in heat exchanger WT1b. The triglycerides, dissolved in the extractant, are thus precipitated to be separated in regenerating column 2. The triglycerides obtained as bottom product P2 are withdrawn; part of the triglycerides is divided off as recycle stream R1 which, after having passed through heat exchanger WT1a, is fed into the head of separating column 1. The cycle gas leaving regenerating column 2 passes through heat exchanger WT2 and is fed into separating column 1 at a point above the bottom section by means of compressor K1.

The bottom product P1 from column 1 comprises monoglycerides and diglycerides and is introduced by means of a compressor into separating column 3 as a feed stream. Pressure and temperature in separating column 3 are chosen such that the diglycerides dissolve preferably in the circulating extractant. At the same time, the extractant dissolves in the downward flowing liquid phase which gradually becomes enriched in monoglycerides. The extractant, loaded with the more easily soluble diglycerides, leaves the amplifying section at the head of countercurrent column 3. The extractant thus loaded is expanded by pressure relief valve EV2 and heated in heat exchanger WT3b, the dissolved triglycerides thus being precipitated in form of droplets. In regenerating column 4, the condensed phase is separated from the extractant. Part of the condensed phase, after having passed through heat exchanger WT3a, is fed back to the head of column 3 as recycle stream R2, the remainder being withdrawn as product P4. The regenerated cycle gas leaves the regenerating column 4 at the head and, after having passed through heat exchanger WT4, is recycled by means of cycle gas compressor K2 into column 3 at a point above the bottom section, The monoglycerides are obtained as bottom product P3 in column 3.

The three different products P2, P3, P4 thus obtained are continuously withdrawn and collected in containers under expansion to atmospheric pressure. The gaseous extractant thus released is returned by means of a compressor into the streams of cycle gas.

When operation takes place under isothermal conditions, the pressure in column 3 is raised by about 5 to 60 bar, preferably by 15 to 40 bar, over the pressure in column 1. For operation under isobaric conditions, the temperature in column 3 is lowered by 10° to 80° C., preferably by 20° to 50° C., as compared to the temperature in column 1, i.e. the density of the extractant in column 3 is raised over that in column 1. The same effect may be achieved by a combination of reduction in temperature and increase in pressure.

To prevent the formation of a single phase due to the decreasing content in difficultly soluble components in the concentration sections of the columns, it is advisable to raise the temperature in the column head over that at the bottom of the column. Depending on the composition of the mixture of glycerides with respect to the involved fatty acids, a temperature difference between head and bottom of from 5° to 40° C., preferably of from 10° to 30° C., is advantageous.

In the above described embodiments, the mixture of glycerides and, respectively, of glycerol-containing glycerides is preferably fed into the middle sections of the various columns. In principle, however, feeding into the head of the respective column or, in some embodiments, at a point between bottom and middle section of the column is also possible.

The process of the invention may also be conducted with the aid of pressure pulsation. The pulsation device is preferably disposed above the bottom section of the separating column. It is a piston device with a straight-motion crank gear. A ratio of displaced volume to column volume between 1:40 and 1:200 is quite favorable for the process of the invention. The pulsation device is provided not only with variable stroke adjusting means but also with frequency control means, thus offering optimum adaptability to the various conditions. Volume displacement effected within the fluid-pulsator is sinusoidal.

In principle, any packings conventionally used in liquid-liquid extraction and rectification techniques, such as Raschig rings, packings of wire netting or wire gauze, saddels wire coils and the like, are suited for the columns used in the process of the invention. Particularly good results are achieved with packings of orderly arranged wire netting such as Sulzer CY. The columns may also be equipped with perforated plates.

EXAMPLE 1

A mixture of glycerides, comprising 59% by weight of monoglycerides, 36% by weight of diglycerides, 4.6% by weight of triglycerides of oleic acid, and 0.4% by weight of free fatty acids, was pumped into the head of a countercurrent column at a temperature of 20° C. and a pressure of 300 bar (density being 450 kg/m$^3$) and subjected to extraction, using pure ethane as extractant. The column had a height of 6 meters and was packed with a wire netting Sulzer CY. The extractant leaving the head of the column showed a loading of 0.66% by weight.

The stream of extractant leaving the separating column was fed into the middle section of the regenerating column. Regeneration conditions were 54 bar and 102° C. (the density of ethane under these conditions being 66 kg/m$^3$). Due to pressure reduction and simultaneous raising of the temperature, loading of the extractant decreased to 0.02% by weight. The regenerated extractant was cooled to 20° C. With the aid of a circulation compressor, it was recycled into the separating column at a point above the bottom section.

The bottom product thus obtained contained 91% by weight of monoglycerides, 8.5% by weight of diglycerides and 0.5% by weight of free fatty acids. Concentration of triglycerides was below the limit of detection of 0.1% by weight. The product from the regenerating column contained 21.3% by weight of monoglycerides, 68% by weight of diglycerides, 10% by weight of triglycerides, and 0.7% by weight of free fatty acids.

EXAMPLE 2

A mixture of glycerides, comprising 61% by weight of monoglycerides, 35% by weight of diglycerides, 3.5% by weight of triglycerides of stearic acid, and 0.5% by weight of free fatty acids, was pumped at a temperature of 110° C. and a pressure of 85 bar into the head of a countercurrent column and extracted therein with propane as extractant. Density of the propane under these conditions was 366 kg/m$^3$. The column had a height of 6 meters and was provided with a Sulzer CY-packing of wire netting. When leaving the column head, the extractant had a loading of 3.8% by weight. The stream of extractant leaving the column head was fed into the middle section of the regenerating column. Conditions of regeneration were 35 bar and 120° C. Under these conditions, propane had a density of 66 kg/m$^3$. By lowering pressure and simultaneously raising the temperature, loading of the extractant was reduced to 0.04% by weight. After having been cooled to 100° C., the regenerated extractant was recycled into the extracting column at a point above the bottom section by means of a compressor.

The bottom product from the separating column contained 99% by weight of monoglycerides, 0.7% by weight of diglycerides, and 0.3% by weight of free fatty acids. Triglyceride concentration was below the detectable limit of 0.1% by weight. The product from the regenerating column contained 31.5% by weight of monoglycerides, 61.6% by weight of diglycerides, 6.2% by weight of triglycerides, and 0.7% by weight of free fatty acids.

EXAMPLE 3

A mixture of glycerides, comprising 50% by weight of monoglycerides, 37.5% by weight of diglycerides, 11% by weight of triglycerides of stearic acid, as well as 1.5% by weight of free fatty acids, was pumped at a temperature of 100° C. and a pressure of 140 bar into the head of a countercurrent column, where it was extracted with a mixture of ethane and propane. Under the above conditions, the extractant having a propane content of 60% by weight was supercritical, i.e. present as a single phase. Its density was 354 kg/m$^3$. The column had a height of 12 meters and was equipped with a Sulzer CY-packing of wire netting. The extractant leaving at the head of the column showed a loading of 1.2% by weight.

The stream of extractant, leaving the head of the separating column, was fed into the middle section of the regenerating column while being expanded to 40 bar and heated to 120° C. Thus, loading of the extractant with glycerides and free fatty acids was reduced to 0.03% by weight. Under these conditions, the extractant had a density of 57 kg/m$^3$.

The regenerated extractant was cooled to 100° C. By means of a circulation compressor, it was fed into the countercurrent column at a point above the bottom section.

The product, withdrawn from the bottoms of the extracting column, contained 85% by weight of monoglycerides, 12% by weight of diglycerides, 2% by weight of triglycerides, and 1% by weight of free fatty acids. The product from the regenerating column contained 35% by weight of monoglycerides, 48% by weight of diglycerides, 15% by weight of triglycerides, and 2% by weight of free fatty acids.

EXAMPLE 4

A mixture of glycerides, comprising 59% by weight of monoglycerides, 36% by weight of diglycerides, 4.3% by weight of triglycerides of oleic acid, and 0.7% by weight of free fatty acids, was pumped at a temperature of 60° C. and a pressure of 80 bar into the head of a countercurrent column, where it was extracted with propane. Its density under the above conditions was 465 kg/m$^3$.

The column had a height of 6 meters and was provided with a Sulzer CY-packing of wire netting. Loading of the extractant with difficultly volatiles was 5.7% by weight.

The stream of extractant leaving the column head was fed into the middle section of the regenerating column. Regeneration conditions were 35 bar and 100° C. the propane having a density of 83 kg/m$^3$ under these conditions. By simultaneously lowering the pressure and raising the temperature, loading of the extractant was reduced to 0.06% by weight. The regenerated extractant was cooled to 60° C. and, by means of a circulation compressor, recycled into the extracting column at a point above the bottom section.

The bottom product from the separating column contained 99.5% by weight of monoglycerides, 0.3% by weight of diglycerides and 0.2% by weight of free fatty acids. Concentration of triglycerides was below the detectable limit of 0.1% by weight. The product from the regenerating column contained 9.5% by weight of monoglycerides, 80.5% by weight of diglycerides, 9% by weight of triglycerides, and 1% by weight of free fatty acids.

EXAMPLE 5

A mixture of glycerides, comprising 58% by weight of monoglycerides, 38% by weight of diglycerides, 3.5% by weight of triglycerides of stearic acid, and 0.5% by weight of free fatty acids, was pumped at a temperature of 110° C. and a pressure of 85 bar into a countercurrent column at a point 1 meter above the bottom and subjected therein to extraction. Pure propane was used as extractant. Its density under the above conditions was 370 kg/m$^3$. The column had a height of 6 meters and was provided with a Sulzer CY-packing of wire netting. Loading of the extractant with glycerides was 4% by weight.

The stream of extractant leaving the column head was fed into the regenerating column. Regeneration conditions were 34.5 bar and 120° C. Under these conditions, the propane had a density of 66 kg/m$^3$. By simultaneously lowering the pressure and heating, loading of the extractant was reduced to 0.04% by weight.

The extractant thus regenerated was cooled to 100° C. and recycled to the bottom of the extracting column by means of a circulation compressor.

Part of the product obtained in the regenerating column was pumped back to the head of the separating column.

The product from the regenerating column contained 5% by weight of monoglycerides, 51.5% by weight of diglycerides, 42% by weight of triglycerides, and 1.5% by weight of free fatty acids.

The bottom product thus obtained contained 62.8% by weight of monoglycerides, 36.8% by weight of diglycerides, and 0.4% by weight of free fatty acids. The concentration of triglycerides was near the lowest detectable limit of 0.1% by weight.

In a second partial step, the bottom product from the first column was pumped at a temperature of 110° C. and a pressure of 85 bar into the middle section of a second countercurrent column and subjected therein to extraction. Again, pure propane served as an extractant. The column had a height of 12 meters and was provided with a Sulzer CY-packing of wire netting. Loading of the extractant with glycerides was 3.4% by weight.

The stream of extractant leaving at the head of the second separating column was fed into the second regenerating column. Regeneration conditions were 34.5 bar and 120° C. By simultaneously lowering the pressure and heating, loading of the extractant was reduced to 0.04% by weight.

The extractant thus regenerated was cooled to 100° C. and fed to the bottom of the second extracting column by means of a second circulation compressor.

Part of the product obtained in the second regenerating column was recycled to the head of the second separating column.

The product from the regenerating column contained 7.4% by weight of monoglycerides, 90% by weight of diglycerides, and 0.6% by weight of free fatty acids. Concentration of triglycerides was 2% by weight.

The bottom product contained 99% by weight of monoglycerides, 0.7% by weight of diglycerides and 0.3% by weight of free fatty acids. Concentration of the triglycerides was below the still detectable limit of 0.1% by weight.

It will be understood that each of the steps, conditions and reagents described above, or two or more together, may also find a useful application in other types of reactions, recovery procedure and products differing from the types described above.

While the invention has been illustrated and described as embodied in the context of a process for preparing pure monoglycerides, pure diglycerides and/or pure triglycerides, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A process for recovering a member selected of the group consisting of monoglycerides, diglycerides, triglycerides, glycerol and mixtures thereof from mixtures of glycerides and glycerol containing mixtures of glycerides comprising the step extracting said mixtures of glycerides and glycerol containing mixtures of glycerides under suitable conditions of temperature and pressure and under countercurrent conditions in a vessel while using a circulating extractant forming a separate phase, wherein the extractant essentially consists of one or more hydrocarbons having a carbon atom chain with at least three carbon atoms, and wherein the extractant has a density of more than 180 kg/m$^3$.

2. A process for recovering a member selected of the group consisting of monoglycerides, diglycerides, triglycerides, glycerol and mixtures thereof from mixtures of glycerides and glycerol containing mixtures of glycerides comprising the step extracting said mixtures of glycerides and glycerol containing mixtures of glycerides under suitable conditions of temperature and pressure and under countercurrent conditions in a vessel while using a circulating extractant forming a separate phase in an absence of a supercritical component of poor solubility, wherein the extractant comprises a hydrocarbon having a carbon atom chain with at least three carbon atoms, and wherein the extractant has a density of more than 180 kg/m$^3$.

3. The process according to claim 2, wherein the hydrocarbons have a density of from about 200 kg/m$^3$ to 800 kg/m$^3$.

4. The process according to claim 2, wherein the hydrocarbons are selected from a member of the group consisting of propane, butane, pentane, and mixtures thereof.

5. The process according to claim 2, wherein the monoglycerides and the diglycerides are recovered as a bottom product from a separating column and an extract phase comprising the triglycerides is drawn off at a head of said separating column.

6. The process according to claim 2, comprising separating an extract phase enriched in the diglycerides and the triglycerides into the various glycerides by stepwise reduction of a density in at least one further subsequent fractionating column.

7. The process according to claim 5, further comprising feeding the bottom product comprising the monoglycerides and the diglycerides into a further separating column.

8. The process according to claim 2, wherein, from a glycerol-containing mixture of glycerides, the glycerol and the monoglycerides are obtained in a first countercurrent column as a bottom product, and the diglycerides and the triglycerides, obtained from a head product after precipitation from the extractant, are transferred to a second countercurrent column with a separate closed cycle for further separation, the diglycerides being drawn off from that column as a bottom product and the triglycerides as a head product.

9. The process according to claim 8, further comprising separating the glycerol from the monoglycerides.

10. The process according to claim 8, wherein part of the products obtained from the head products of the first and the second countercurrent columns is fed as a recycle stream into the head of the respective column.

11. The process according to claim 2, wherein the extracting under countercurrent conditions is conducted in a packed column under pressure pulsation.

12. The process according to claim 2, wherein the extracting under countercurrent conditions is conducted in a column provided with perforated plates without a flow off shaft, and wherein a downwards flowing liquid phase is transported through said perforated plates by means of pressure pulsation.

13. The process according to claim 2, wherein the extracting under countercurrent conditions is conducted in a rotating disk column.

14. The process according to claim 7, further comprising feeding the extract phase of the separating column after separation of the monoglycerides into a subsequent fractionating column and withdrawing the diglycerides after density reduction of the extractant as a bottom product from said fractionating column.

15. The process according to claim 14, further comprising feeding a head product of said first fractionating column comprising the triglycerides into a second fractionating column and separating the triglycerides after further density reduction from said second fractionating column.

16. The process according to claim 15, further comprising feeding a portion of each bottom product formed in the fractionating columns as a recycle stream into the head of the preceding column.

17. A process for separating mixtures of fatty acid glycerides and mixtures of fatty acid glycerides and glycerol and recovering a member selected from the group consisting of monoglycerides, diglycerides, triglycerides, and glycerol and mixtures thereof, by contacting mixtures of said glycerides or said glycerides and glycerol, liquid under process conditions, in a separating column in countercurrent with a circulating extractant forming a separate phase, wherein the extractant is free of an entrainer and essentially consists of a hydrocarbon having a carbon atom chain with at least three carbon atoms in the carbon atom chain, and mixtures thereof, and wherein the extraction is carried out at temperatures of from about 10° C. to about 160° C. and at a pressure chosen such that the hydrocarbon extractant has a density of from about 180 kg/m$^3$ to 800 kg/m$^3$ to obtain a bottom product enriched in monoglycerides and an extract phase comprising diglycerides and triglycerides.

18. The process according to claim 17, wherein the hydrocarbon has a density of from about 200 kg/m$^3$ to 800 kg/m$^3$.

19. The process according to claim 17, wherein the hydrocarbon is selected from a member of the group consisting of propane, butane, pentane, and mixtures thereof.

20. The process according to claim 17, wherein monoglycerides and diglycerides are recovered as a bottom product from the separating column and an extract phase comprising triglycerides is drawn off at the head of said separating column.

21. The process according to claim 17, comprising separating the extract phase enriched in diglycerides and triglycerides into the various glycerides by stepwise reduction of the density in at least one further subsequent fractionating column.

22. The process according to claim 20, further comprising feeding the bottom product comprising monoglycerides and diglycerides into a further separating column.

23. The process according to claim 17, wherein, from a glycerol-containing mixture of glycerides, glycerol and monoglycerides are obtained in a first countercurrent column as a bottom product, and the diglycerides and triglycerides, obtained from the head product after precipitation from the extractant, are transferred to a second countercurrent column with a separate closed cycle for further separation, the diglycerides being drawn off from that column as the bottom product and the triglycerides as the head product.

24. The process according to claim 23, further comprising separating glycerol from the monoglycerides.

25. The process according to claim 23, wherein part of the products obtained from the head products of the countercurrent columns is fed as a recycle stream into the head of the respective column.

26. The process according to claim 17, wherein the extracting under countercurrent conditions is conducted in a packed column under pressure pulsation.

27. The process according to claim 17, wherein the extracting under countercurrent conditions is conducted in a column provided with perforated plates without a flow off shaft, and wherein a downwards flowing liquid phase is transported through said perforated plates by means of pressure pulsation.

28. The process according to claim 17, wherein the extracting under countercurrent conditions is conducted in a rotating disk column.

29. A process for separating mixtures of fatty acid glycerides and recovering a member selected from the group consisting of monoglycerides, diglycerides and triglycerides and mixtures thereof, by contacting mixtures of said glycerides, liquid under process conditions, in a separating column in countercurrent with a circulating extractant forming a separate phase, wherein the extractant is free of an entrainer and essentially consists of a hydrocarbon having a carbon atom chain with at least three carbon atoms in the carbon atom chain, and mixtures thereof, and wherein the extraction is carried out at temperatures of from about 10° C. to about 160° C. and at a pressure chosen such that the hydrocarbon extractant has a density of from about 180 kg/m$^3$ to 800 kg/m$^3$ to obtain a bottom product essentially pure in monoglycerides and an extract phase comprising diglycerides and triglycerides.

30. The process according to claim 29, wherein the hydrocarbon is selected from a member of the group consisting of propane, butane, pentane, and mixtures thereof.

31. The process according to claim 29, further comprising feeding the extract phase of the separating column after separation of the monoglycerides into a subsequent fractionating column and withdrawing the diglycerides after density reduction of the extractant as a bottom product from said fractionating column.

32. The process according to claim 31, further comprising feeding the top product of said first fractionating column comprising the triglycerides into a second fractionating column and separating the triglycerides after further density reduction from said second fractionating column.

33. The process according to claim 32, further comprising feeding a portion of each bottom product formed in the fractionating columns as a recycle stream into the head of the preceding column.

34. A process for separating mixtures of fatty acid glycerides and mixtures of fatty acid glycerides and glycerol and recovering a member selected from the group consisting of monoglycerides, diglycerides, triglycerides, glycerol and mixtures thereof by contacting mixtures of said glycerides and said glycerides and glycerol, liquid under process conditions, in a separating column in countercurrent with a circulating extractant forming a separate phase, wherein the extractant is free of an entrainer and essentially consists of a member selected from the group consisting of propane, butane and mixtures thereof, and wherein the extraction is carried out at temperatures of from about 10° C. to about 160° C. and at pressures chosen such that the hydrocarbon extractant has a density of from about 180 kg/m$^3$ to 800 kg/m$^3$ to separate a product enriched in monoglycerides and an extract phase enriched in diglycerides and triglycerides.

35. The process according to claim 34, wherein propane is used as an extractant and wherein the extraction is carried out at pressures of up to 250 bar.

36. A process for separating mixtures of fatty acid glycerides and mixtures of fatty acid glycerides and glycerol and recovering a member selected from the group consisting of monoglycerides, diglycerides, triglycerides, glycerol and mixtures thereof by contacting mixtures of said glycerides and said glycerides and glycerol, liquid under process conditions, in a packed column under pressure pulsation in countercurrent with a circulating extractant forming a separate phase, wherein the extractant is free of an entrainer and essentially consists of a member selected from the group consisting of propane, butane, pentane, and mixtures thereof, and the extraction is carried out in a temperature range of from about 10° C. to about 160° C. and at pressures up to 250 bar such that the hydrocarbon extractant has a density of from about 180 kg/m$^3$ to 800 kg/m$^3$, further comprising separating a bottom product enriched in monoglycerides in a separating column, feeding the remaining extract enriched in diglycerides and triglycerides obtained as head product of the separating column into a subsequent fractionating column, separating the diglycerides after density reduction of the extractant as a bottom product from said fractionating column, feeding the head product of said first fractionating column comprising the triglycerides in a second fractionating column, separating the triglycerides after further density reduction from said second fractionating column, and feeding a portion of each bottom product formed in the fractionating columns as a recycle stream into the head of the preceding column.

37. A process for separating mixtures of fatty acid glycerides and mixtures of fatty acid glycerides and glycerol and recovering a member selected from the group consisting of monoglycerides, diglycerides, triglycerides, glycerol and mixtures thereof by contacting mixtures of said glycerides and said glycerides and glycerol, liquid under process conditions, in a column forming a vessel provided with perforated plates without a flow off shaft, wherein a downwards flowing liquid phase is transported through said perforated plates by means of pressure pulsation, in countercurrent with a circulating extractant forming a separate phase, wherein the extractant essentially consists of butane, and the extraction is carried out in a temperature range of from about 10° C. to about 160° C. and at pressures up to 250 bar such that the hydrocarbon extractant has a density of from about 180 kg/m$^3$ to 800 kg/m$^3$, further comprising separating a bottom product in a separating column, wherein pure monoglycerides are obtained as bottom product, drawing off the extract comprising diglycerides and triglycerides at the head of the separating column, feeding the head product after separation of the monoglycerides into a subsequent fractionating column, separating the diglycerides after density reduction of the extractant as a bottom product from said fractionating column, separating the triglycerides from the head product of said first fractionating column in a second fractionating column under further density reduction, and feeding a portion of each bottom product formed in the fractionating column(s) as a recycle stream into the head of the preceding column.

* * * * *